United States Patent
Govari et al.

(10) Patent No.: US 11,478,182 B2
(45) Date of Patent: Oct. 25, 2022

(54) INCORPORATING A CONFIDENCE LEVEL INTO AN ELECTROPHYSIOLOGICAL (EP) MAP

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/144,029

(22) Filed: Jan. 7, 2021

(65) Prior Publication Data
US 2022/0211314 A1 Jul. 7, 2022

(51) Int. Cl.
| | |
|---|---|
| A61B 5/367 | (2021.01) |
| G16H 50/50 | (2018.01) |
| G06T 19/00 | (2011.01) |
| A61B 5/00 | (2006.01) |
| A61B 5/343 | (2021.01) |
| A61B 5/346 | (2021.01) |
| A61B 5/287 | (2021.01) |

(52) U.S. Cl.
CPC .............. *A61B 5/367* (2021.01); *A61B 5/343* (2021.01); *A61B 5/346* (2021.01); *A61B 5/7221* (2013.01); *G06T 19/00* (2013.01); *G16H 50/50* (2018.01); *A61B 5/287* (2021.01); *G06T 2210/41* (2013.01); *G06T 2219/004* (2013.01)

(58) Field of Classification Search
CPC ......... A61B 5/367; A61B 5/346; A61B 5/343; A61B 5/7221; A61B 5/287; A61B 5/061; A61B 5/339; A61B 5/316; A61B 5/6852; A61B 5/6858; A61B 2017/00053; G16H 50/50; G06T 19/00; G06T 2210/41; G06T 2219/004

See application file for complete search history.

(56) References Cited

U.S. PATENT DOCUMENTS

| | | | |
|---|---|---|---|
| 6,301,496 B1 * | 10/2001 | Reisfeld | G06T 17/20 600/407 |
| 8,103,338 B2 * | 1/2012 | Harlev | A61B 5/0044 600/547 |
| 8,359,092 B2 * | 1/2013 | Hayam | A61B 5/283 600/523 |
| 8,456,182 B2 | 6/2013 | Bar-Tal | |

(Continued)

OTHER PUBLICATIONS

European Search Report for corresponding EPA No. 22150426.9 dated Apr. 29, 2022.

*Primary Examiner* — Abderrahim Merouan
(74) *Attorney, Agent, or Firm* — Dergosits & Noah LLP; Todd A. Noah

(57) ABSTRACT

A method includes receiving (i) a modeled surface of at least a portion of a heart and (ii) multiple EP values measured at multiple respective positions in the heart. Multiple regions are defined on the modeled surface and, for each region, a confidence level is estimated for the EP values whose positions fall in the region. The modeled surface is presented to a user, including (i) the EP values overlaid on the modeled surface, and (ii) the confidence level graphically visualized in each region of the modeled surface.

26 Claims, 4 Drawing Sheets

(56) References Cited

U.S. PATENT DOCUMENTS

| | | | |
|---|---|---|---|
| 8,620,417 B2* | 12/2013 | Turgeman | A61B 5/6869 600/523 |
| 8,948,857 B2 | 2/2015 | Brodnick | |
| 9,532,725 B2 | 1/2017 | Laughner | |
| 9,629,567 B2* | 4/2017 | Porath | A61B 5/349 |
| 10,441,188 B2* | 10/2019 | Katz | A61B 5/6858 |
| 10,588,531 B2 | 3/2020 | Mahapatra | |
| 11,160,485 B2* | 11/2021 | Botzer | A61B 5/333 |
| 2007/0197929 A1* | 8/2007 | Porath | A61B 5/349 600/523 |
| 2007/0208260 A1* | 9/2007 | Afonso | A61B 5/339 600/508 |
| 2007/0223794 A1 | 9/2007 | Preiss | |
| 2013/0296845 A1* | 11/2013 | Bar-Tal | A61B 18/1492 606/34 |
| 2014/0107510 A1* | 4/2014 | Bogun | A61B 5/7485 600/516 |
| 2015/0025351 A1* | 1/2015 | Govari | A61B 5/339 600/374 |
| 2015/0228254 A1 | 8/2015 | Olson | |
| 2015/0250399 A1 | 9/2015 | Laughner | |
| 2015/0257845 A1* | 9/2015 | Gopalakrishna | A61B 34/20 600/424 |
| 2016/0038047 A1* | 2/2016 | Urman | A61B 5/743 600/410 |
| 2017/0042449 A1* | 2/2017 | Deno | A61M 25/0127 |
| 2017/0173391 A1* | 6/2017 | Wiebe | G09B 19/0038 |
| 2018/0307998 A1* | 10/2018 | Strachan | G06K 9/6217 |
| 2020/0256939 A1* | 8/2020 | Wang | G01R 33/4822 |
| 2020/0397327 A1* | 12/2020 | Stewart | A61B 5/339 |
| 2021/0038171 A1* | 2/2021 | Katz | A61B 5/339 |
| 2021/0100612 A1* | 4/2021 | Baron | A61B 5/061 |

* cited by examiner

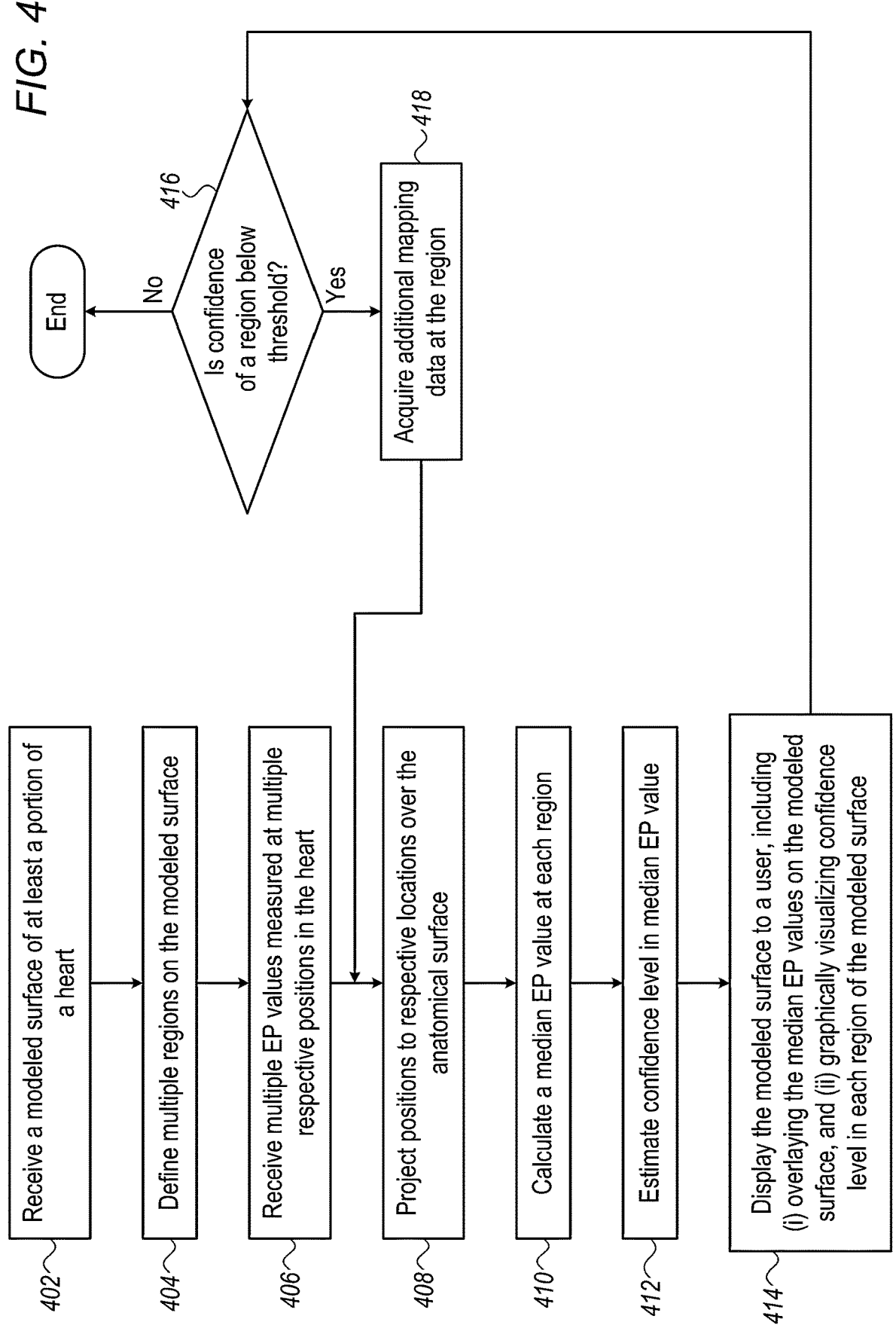

INCORPORATING A CONFIDENCE LEVEL INTO AN ELECTROPHYSIOLOGICAL (EP) MAP

FIELD OF THE INVENTION

The present invention relates generally to electrophysiological mapping, and particularly to visualization of cardiac electrophysiological maps.

BACKGROUND OF THE INVENTION

Electrophysiological (EP) cardiac mapping may use visualizations methods previously proposed in the patent literature, to ease an interpretation of an EP map. For example, U.S. Pat. No. 9,532,725 describes an example medical device that may include a catheter shaft with a plurality of electrodes coupled thereto, and a processor coupled to the catheter shaft. The processor may be capable of collecting a set of signals from the plurality of electrodes and generating a data set from at least one of the set of signals. The data set may include at least one known data point and one or more unknown data points. The processor may also be capable of interpolating at least one of the unknown data points by conditioning the data set, assigning an interpolated value to at least one of the unknown data points, and assigning a confidence level to the interpolated value. In order to convey the confidence of the interpolated data, the derived confidence levels may take the form of a confidence map, so that the confidence level of the interpolated data may be displayed.

As another example, U.S. Pat. No. 6,301,496 describes a method of diagnosing cardiac arrhythmias, including the steps of measuring a physiological response and calculating a vector function related to the response, displaying a representation of the vector function, and inferring the abnormal condition from the representation. The physiological response is a voltage, from which is inferred a local activation time (LAT) and the vector function is a gradient of the local activation time, specifically, a conduction velocity. Measured data may be displayed on the map using a pseudo color scale when a value represents one that is of a determined confidence level and as such, may be placed directly on the pseudo color map; and by another, different color or transparency, when the value is of low confidence and as such, is so displayed. In the latter case, the practitioner will be guided to acquire more samples.

U.S. Patent Application Publication No. 2016/0038047 describes a method, including recording parameters indicative of a quality of ablation performed at one or more sites in a region of a human heart, and receiving a set of electrophysiological signals indicative of a wave of electrical activation flowing through the region. The method further includes identifying locations within the region at which the wave is blocked from flowing and estimating confidence levels with respect to a blockage of the wave at the locations in response to the signals and the parameters. The method also includes displaying a map of the human heart including an indication of the confidence levels.

U.S. Pat. No. 10,588,531 describes systems and methods for determining prevalence of a cardiac phenomenon based on electrophysiological (EP) data from a tissue of a body. One system includes an electronic control unit communicatively coupled to a display device and configured to, for each of the plurality of locations, detect, at each of a plurality of discrete times occurring during a predetermined time period, whether a cardiac phenomenon occurs at the location based on the EP data, determine a prevalence of the cardiac phenomenon based on the detecting, and display information indicative of the determined prevalence of the cardiac phenomenon on the display device. A confidence score associated with the prevalence value may also be determined and displayed. Generally, the longer the predetermined period of time and the higher the sampling frequency, the greater the confidence score.

U.S. Pat. No. 9,629,567 describes software and apparatus to automatically detect and map areas of complex fractionated electrograms within cardiac chambers. Electrogram signal are analyzed to count the number of complexes whose amplitude and peak-to-peak intervals meet certain criteria. Functional maps indicating average complex interval, shortest complex interval, and confidence levels are produced for display. For example, confidence level tags are displayed, corresponding to rate at which complex fractionated electrograms occur at a location during the examination.

SUMMARY OF THE INVENTION

An embodiment of the present invention that is described hereinafter provides a method including receiving (i) a modeled surface of at least a portion of a heart and (ii) multiple EP values measured at multiple respective positions in the heart. Multiple regions are defined on the modeled surface and, for each region, a confidence level is estimated for the EP values whose positions fall in the region. The modeled surface is presented to a user, including (i) the EP values overlaid on the modeled surface, and (ii) the confidence level graphically visualized in each region of the modeled surface.

In some embodiments, estimating the confidence level includes calculating the confidence level depending on a count of the EP values falling in the region. In some embodiments, estimating the confidence level for a region includes calculating the confidence level as an increasing function of a count of the EP values falling in the region. In other embodiments, estimating the confidence level for a region includes calculating the confidence level as a decreasing function of a variance of a distribution of the EP values falling in the region.

In an embodiment, receiving the EP values includes acquiring the EP values using a catheter.

In another embodiment, the modeled surface is a surface generated by fast anatomical mapping (FAM).

In some embodiments, the EP values are one of local activation times (LATs), bipolar potentials, and unipolar potentials.

In some embodiments, an EP value in a region is a median of the EP values in the region.

In an embodiment, graphically visualizing the confidence levels includes presenting, at the regions, respective icons whose sizes are an increasing function of the respective confidence levels.

In another embodiment, the method further includes, in response to detecting that a confidence level of a region is lower than a predefined confidence level threshold, receiving one or more additional EP values for the region and re-estimating the confidence level for the EP values falling in the region, including the one or more additional EP values.

In some embodiments, receiving the EP values for a region includes projecting multiple positions onto multiple locations in the region, and assigning the EP values at the positions to the respective locations.

In some embodiments, the regions include polygons in a polygonal mesh of the modeled surface. In other embodiments, one or more of the regions are circular areas having a predefined radius.

There is additionally provided, in accordance with another embodiment of the present invention, a system including an interface and a processor. The interface is configured to receive (i) a modeled surface of at least a portion of a heart and (ii) multiple EP values measured at multiple respective positions in the heart. The processor is configured to: define multiple regions on the modeled surface and, for each region, estimate a confidence level for the EP values whose positions fall in the region, and display the modeled surface to a user, including (i) overlaying the EP values on the modeled surface, and (ii) graphically visualizing the confidence level in each region of the modeled surface.

BRIEF DESCRIPTION OF THE DRAWINGS

The present invention will be more fully understood from the following detailed description of the embodiments thereof, taken together with the drawings in which:

FIG. 4 is a flow chart that schematically illustrates a method for projecting and graphically visualizing EP values on the EP map of FIG. 2B, in accordance with another exemplary embodiment of the present invention.

DETAILED DESCRIPTION OF EMBODIMENTS

Overview

Figure 1:
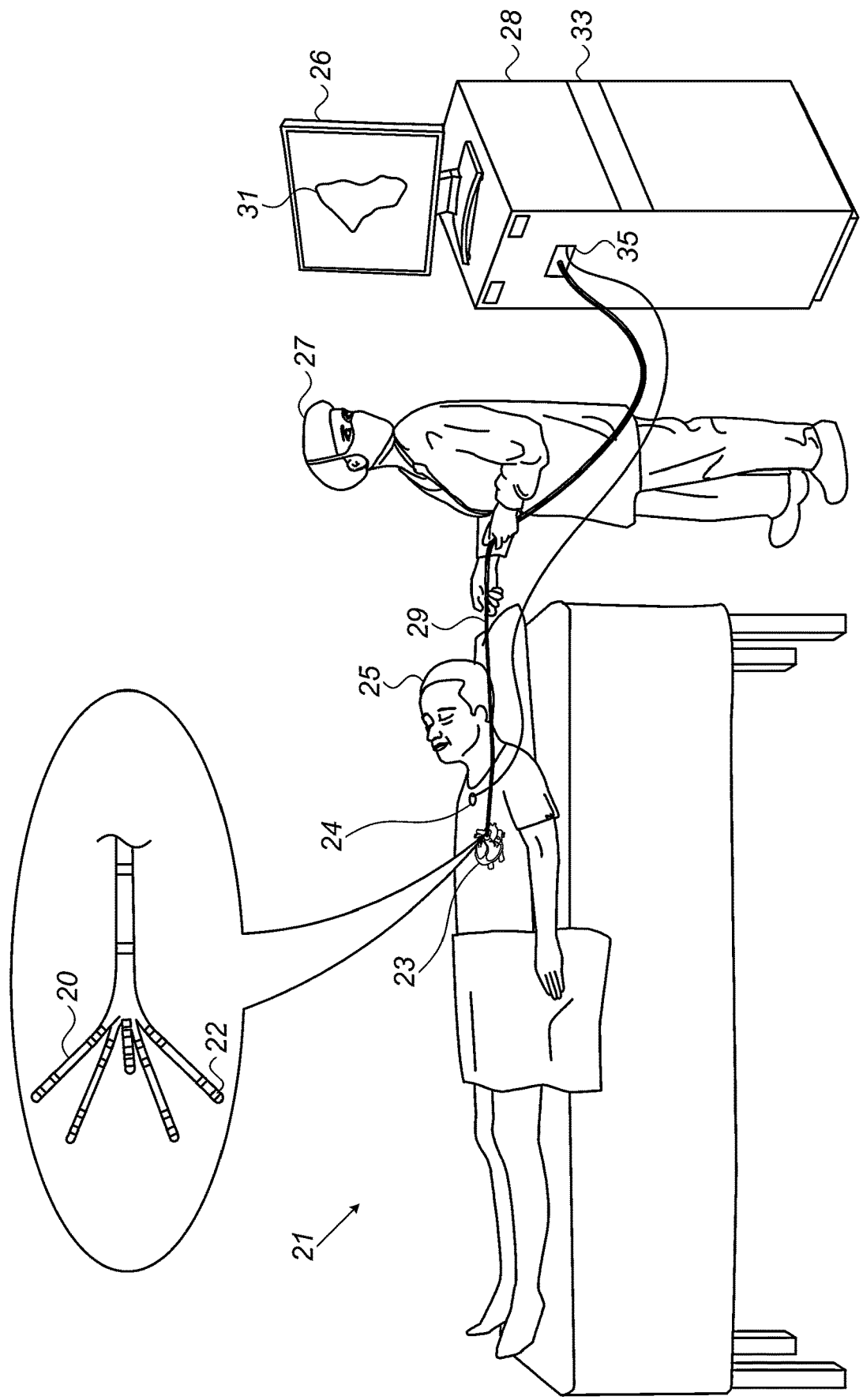
FIG. 1 is a schematic, pictorial illustration of a system for electrophysiological (EP) mapping, in accordance with an exemplary embodiment of the present invention.

Catheter-based electrophysiological (EP) mapping techniques may produce various types of EP maps of an organ, such as a left atrium of a heart. Cardiac EP maps, such as a local activation time (LAT) map, a bipolar potential map, or a unipolar potential map, are produced by acquiring electrograms from locations on a heart chamber surface. EP values, such as LATs (or potentials), are then derived from the electrograms for the locations. Such locations and respective EP values, called hereafter "data points," are then overlayed, typically as a color, onto a 3D map of the chamber.

However, an EP map, which is usually obtained by interpolating over EP values, gives no indication of the quality of a shown EP value. For example, the color of a particular cardiac region may be generated by interpolating LATs of a few locations that are relatively far from the region, or by interpolating LATs of a large number of locations close to or inside the region, or even by finding the LAT of just one location.

In particular, a vast number of data points may be acquired in a short time, especially when using automatic acquisition with a multi electrode catheter, which results in many of the data points being subsequently projected to a same surface region. One existing mapping approach to avoid such a large number of localized acquisition points is to use a density filter. A second approach is for the processor to use only the closest localized acquisition point for map coloring. Neither approach uses all captured data, and therefore cannot prevent incorporating outlier EP values into the EP map.

Embodiments of the present invention that are described hereinafter provide methods and systems to improve map quality of multi-electrode catheter systems that acquire a vast number of data points in a short period of time. To this end, a technique is provided to increase a confidence level for the EP values (e.g., LAT values) shown in the map.

In an embodiment, a processor receives a modeled surface of at least a portion of a heart and multiple EP values measured at multiple respective positions in the heart. The processor defines multiple regions on the modeled surface (e.g., triangles of a triangular mesh) and, for each region, estimates a confidence level for the EP values whose positions fall in the region. The processor displays the modeled surface to a user, including (i) overlaying the EP values on the modeled surface, and (ii) graphically visualizing the confidence level in each region of the modeled surface. In another embodiment, the processor is configured to estimate the confidence level based on a count of the EP values falling in the region.

For example, the processor may calculate an EP value for a given region by averaging a number of measured locations in the region. A region may be a polygon of a polygonal map mesh in a fast anatomical map (FAM) of the chamber. An example of a polygon is a triangle in a triangular mesh. In another embodiment, a region maybe defined as a circle with a preselected radius.

In another embodiment, the processor accepts all measurements (e.g., LAT values). When multiple locations are projected to a same surface region on a map, the processor may calculate a median (or, in some cases, an average) EP value of the set of EP values, to minimize an error in the EP value therein and to avoid outlier values. Thus, estimating a confidence level for the EP values whose positions fall in the region may comprise projecting multiple positions onto multiple locations in the region and calculating the confidence level depending on a count of EP values falling in the region and EP values projected to the region.

The user can also identify areas of the map having lower confidence levels and update the map by acquiring more data points at locations within these areas with the multi-electrode catheter to be processed in a similar way to the one described above, thereby increasing the confidence level therein.

In some embodiments, a method is provided for displaying to a user a confidence level that increase with a count of the total number of acquired data points same in the region (i.e., sum of already located data points therein and once projected). Alternatively, the confidence level is calculated as an inverse of a variance value of the EP values used (e.g., a median one). In the alternative embodiment, a large variance of the EP values in a region causes the processor to assign low confidence level to, for example, a median EP value.

Typically, however, it is expected that a large number of EP values per region will produce a low variance in EP value distribution among data points in the region, and therefore a high confidence level.

The confidence level is presented by overlaying icons (e.g., hexagonal relief, lozenges) at the surface locations on the map, where icons of different sizes (e.g., circles with a different radius) correspond to the counted number of locations used to generate the EP value therein. For example, confidence levels may be grouped into high, medium, and low categories by representing them as large, medium, and small circles, respectively.

Typically, the processor is programmed in software containing a particular algorithm that enables the processor to conduct each of the processor-related steps and functions outlined above.

By increasing confidence level in EP values and displaying confidence level on the map using graphical means, the disclosed techniques may assist the physician in the interpretation of EP maps and thus expedite and improve the quality of complicated diagnostic tasks, such as those required in diagnostic catheterizations.

System Description

FIG. 1 is a schematic, pictorial illustration of a system 21 for electrophysiological (EP) mapping, in accordance with an embodiment of the present invention. FIG. 1 depicts a physician 27 using a mapping Pentaray® catheter 29 to perform an EP mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23. A processor 28 receives these signals via an electrical interface 35, and uses information contained in these signals to construct an EP map 31 stored by processor 28 in a memory 33. During and/or following the procedure, processor 28 may display EP map 31 on a display 26.

EP map 31 may be an LAT map, a bipolar potential map, or another map type. EP map 31 has an improved quality using the disclosed technique to derive and present confidence level on the map, as described in FIGS. 2A and 2B and FIG. 3.

During the procedure, a tracking system is used to track the respective locations of sensing electrodes 22, such that each of the signals may be associated with the location at which the signal was acquired. For example, the Active Catheter Location (ACL) system, made by Biosense-Webster (Irvine Calif.), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface electrodes 24 that are coupled to the skin of patient 25. For example, three surface electrodes 24 may be coupled to the patient's chest and another three surface electrodes may be coupled to the patient's back. (For ease of illustration, only one surface electrode is shown in FIG. 1.) Electric currents are passed between electrodes 22 inside heart 23 of the patient and surface-electrodes 24. Processor 28 calculates an estimated location of all electrodes 22 within the patient's heart based on the ratios between the resulting current amplitudes measured at surface electrodes 24 (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals. Other types of sensing catheters, such as the Lasso® Catheter (produced by Biosense Webster) or basket catheters may equivalently be employed. Physical contact sensors may be fitted at the distal end of mapping catheter to estimate contact quality between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Overlaying a Confidence Level on an Ep Map

Figure 2B:
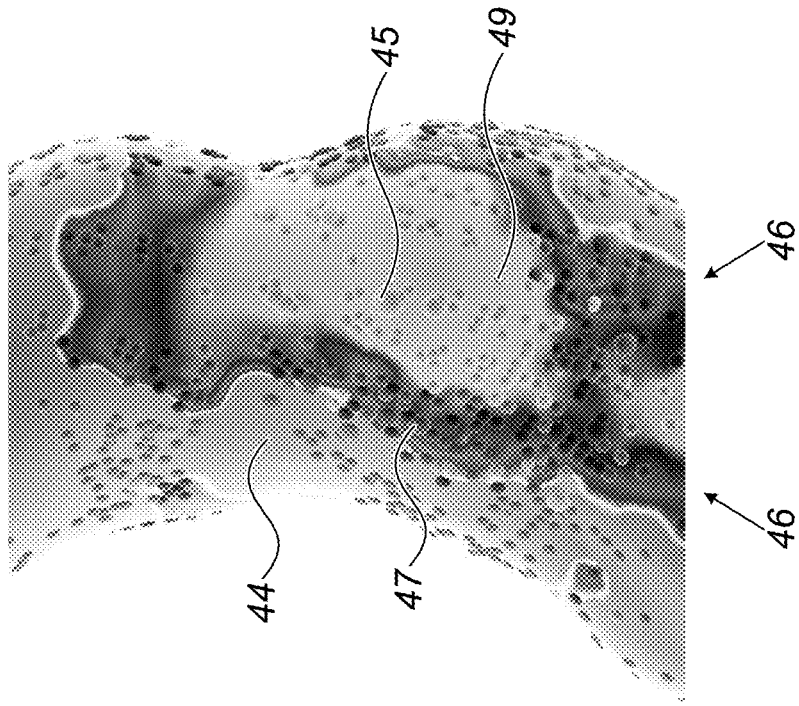
FIGS. 2A and 2B are schematic, pictorial volume renderings of, respectively, an EP map of a right atrium overlaid with original EP values, and a regenerated EP map of the right atrium overlaid with graphically visualized EP values, in accordance with an exemplary embodiment of the present invention.
Figure 2A:
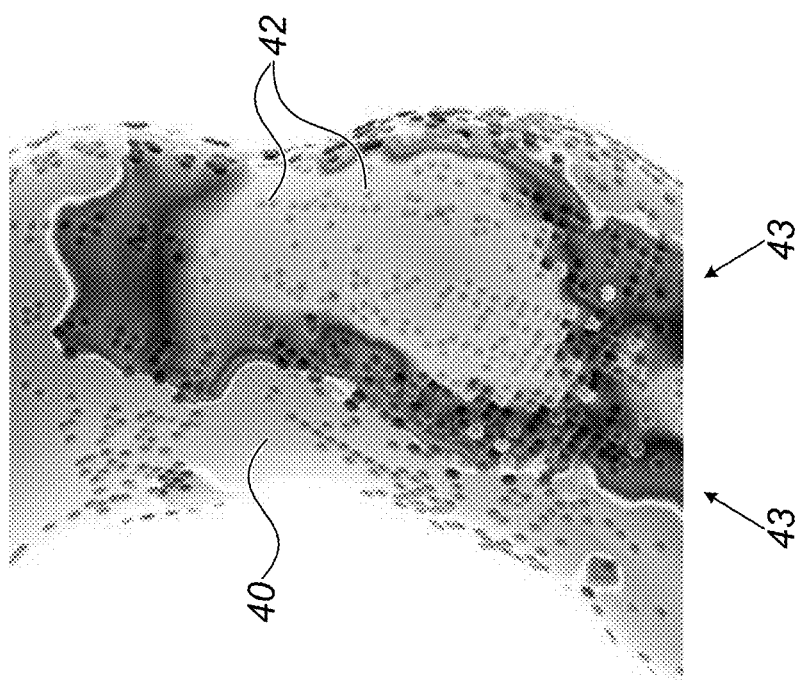

FIGS. 2A and 2B are schematic, pictorial volume renderings of, respectively, an EP map 40 of a right atrium overlaid with original EP values 42, and a regenerated EP map 44 of the right atrium overlaid with graphically visualized EP values (45, 47, 49) in accordance with an embodiment of the present invention.

In map 40, EP values 42 may fall on a same or very similar location, and existing methods do not utilize this information to increase map reliability, as described above.

In the disclosed technique, EP map 44 is generated using median EP values at surface regions, taking the number of data points per the region into account to increase map reliability.

In the shown map 44, three possible confidence levels of EP values are assigned with a surface region. As seen, an EP value with a high confidence level is marked by a large size icon 49, an EP value with a medium confidence level is marked by a medium size icon 47, and an EP value with a low confidence level is marked by a small size icon 45.

As can be seen, regenerated EP map 44 has also modified contours 46 relative to contours 43 of EP map 40. The new contours reflect changed interpolated EP values. The changed interpolation values are derived using the assigned data points (e.g., using EP values which may be median EP values per region or per location).

While FIG. 2A/B show the confidence levels in the form of different relief hexagon sizes, the confidence levels may be presented by another graphical means, such as color coding. Furthermore, while FIG. 2A/B show a dual-layer EP map, the disclosed technique may overlay the confidence levels on a multilayer map, of which at least one may not be an EP map, for example, a cardiac chamber wall thickness map.

Figure 3:
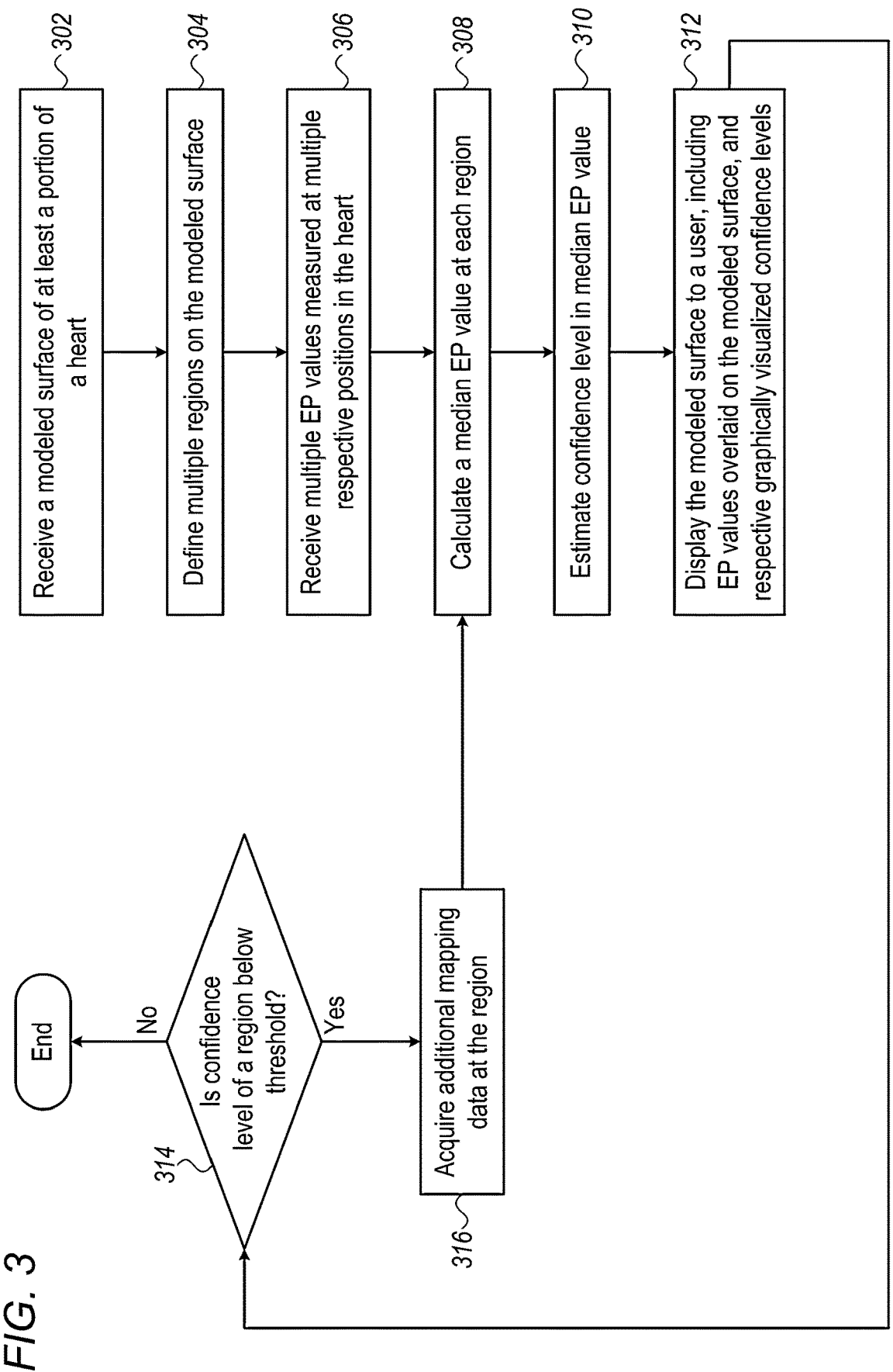
FIG. 3 is a flow chart that schematically illustrates a method for estimating and graphically visualizing EP values on the EP map of FIG. 2B, in accordance with an exemplary embodiment of the present invention.

FIG. 3 is a flow chart that schematically illustrates a method for estimating and graphically visualizing EP values on the EP map of FIG. 2B, in accordance with an embodiment of the present invention. The algorithm, according to the presented embodiment, carries out a process that begins with processor 28 receiving a modeled surface (e.g., an anatomical map) of at least a portion of a heart, at a model receiving step 302.

The processor defines multiple regions (e.g., triangles) on the modeled surface, at a regions defining step 304.

At a data-points receiving step 306, The processor revives multiple data points comprising EP values measured at multiple respective positions associated with the modeled surface. Step 306 may include all or part of the separate steps of acquiring electrograms using a multi-electrode catheter and processor 28 analyzing electrograms to derive EP values, such as LAT values.

Next, at an EP values calculation step 308, processor 28 calculates a median EP value at each region.

Using the number of median EP values at each region, processor 28 estimates a confidence level in the median EP value at each region, at a confidence level estimation step 310.

At an EP map presentation step 312, processor 28 presents the modeled surface with the median EP values overlaid, and with graphically visualized confidence levels of the EP value at each region, e.g., by overlying an icon at the region, where the icon graphics (e.g., size) is indicative of the confidence level therein.

At EP map updating steps, a user or a processor may identify regions of the map having lower confidence levels and update the map. At a map checking step 314, the user identifies regions of the map having lower confidence levels than, for example, a predefined threshold level.

If the user (or the processor) finds a region with a confidence level lower than a predefined threshold level, the user may use the mapping system to acquire more data points with the multi-electrode catheter at locations within the region, at an additional acquisition step 316.

The additional data points acquired at positions associated within these regions are added to the available ones, to be reprocessed by the algorithm by returning to step 308.

As noted above, data points can be projected onto the surface to add confidence and remove outliers.

FIG. 4 is a flow chart that schematically illustrates a method for projecting and graphically visualizing EP values on the EP map of FIG. 2B, in accordance with another embodiment of the present invention. The algorithm, according to the presented embodiment, carries out a process that begins with processor 28 receiving a modeled surface (e.g., an anatomical map) of at least a portion of a heart, at a model receiving step 402.

The processor defines multiple regions (e.g., triangles) on the modeled surface, at a regions defining step 404.

At a data-points receiving step 406, the processor revives multiple data points comprising EP values measured at multiple respective positions associated with the modeled surface. Step 406 may include all or part of the separate steps of acquiring electrograms using a multi-electrode catheter and processor 28 analyzing electrograms to derive EP values, such as LAT values.

Next, processor 28 projects the multiple respective positions onto multiple locations over the modeled surface, at a data points projection step 408. For data points already on the surface no actual projection occurs.

Next, at an EP values calculation step 410, processor 28 calculates a median EP value at each region.

Using the number of median EP values at each region, processor 28 estimates a confidence level in the median EP value at each region, at a confidence level estimation step 412.

At an EP map presentation step 414, processor 28 presents the modeled surface with the median EP values overlaid, and with graphically visualized confidence levels of the EP value at each region, e.g., by overlying an icon at the region, where the icon graphics (e.g., size) is indicative of the confidence level therein.

At EP map updating steps, a user or a processor may identify regions of the map having lower confidence levels and update the map. At a map checking step 416, the user identifies regions of the map having lower confidence levels than, for example, a predefined threshold level.

If the user (or the processor) finds a region with a confidence level lower than a predefined threshold level, the user may use the mapping system to acquire more data points with the multi-electrode catheter at locations within the region, at an additional acquisition step 418.

The additional data points acquired at positions associated within these regions are added to the available ones, to be reprocessed by the algorithm by returning to step 408.

The example flow charts shown in FIGS. 3 and 4 are chosen purely for the sake of conceptual clarity. In optional embodiments, various additional steps may be performed, for example to automatically register additional layers, such as of medical images, and to generate a display that can toggle among all layers.

Although the embodiments described herein mainly address cardiac applications, the methods and systems described herein can also be used in other applications, such as in electroanatomical mapping of a brain.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for incorporating a confidence level into an electrophysiological ("EP") map, comprising:
    receiving a modeled surface of at least a portion of a heart and multiple EP values measured at multiple respective positions in the heart;
    defining multiple regions on the modeled surface;
    calculating a median EP value for each of the multiple regions based upon the measured EP values whose positions fall in the region;
    estimating a confidence level for each of the median EP values;
    causing the modeled surface to be displayed to a user, including median EP values overlaid on the modeled surface, and respective graphically visualizing the confidence levels for the EP values at each region of the modeled surface;
    identifying each region of the multiple regions having a confidence level lower than a predefined threshold level;
    acquiring one or more additional EP values at additional locations within each region having confidence levels lower than the threshold; and
    using the one or more additional EP values to recalculate the median EP value and confidence level for the recalculated median EP value for each region having confidence levels lower than the threshold until the respective confidence level for each region equals or exceeds the threshold.

2. The method according to claim 1, wherein estimating the confidence level comprises calculating the confidence level depending on a count of the EP values falling in the region.

3. The method according to claim 1, wherein estimating the confidence level for a region comprises calculating the confidence level as an increasing function of a count of the EP values falling in the region.

4. The method according to claim 1, wherein estimating the confidence level for a region comprises calculating the confidence level as a decreasing function of a variance of a distribution of the EP values falling in the region.

5. The method according to claim 1, wherein receiving the EP values comprises acquiring the EP values using a catheter.

6. The method according to claim 1, wherein the modeled surface is a surface generated by fast anatomical mapping (FAM).

7. The method according to claim 1, wherein the EP values are one of local activation times (LATs), bipolar potentials, and unipolar potentials.

8. The method according to claim 1, wherein graphically visualizing the confidence levels comprises presenting, at the regions, respective icons whose sizes are an increasing function of the respective confidence levels.

9. The method according to claim 1, wherein receiving the EP values for a region comprises projecting multiple positions onto multiple locations in the region, and assigning the EP values at the positions to the respective locations.

10. The method according to claim 1, wherein the regions comprise polygons in a polygonal mesh of the modeled surface.

11. The method according to claim 1, wherein one or more of the regions are circular areas having a predefined radius.

12. A system for incorporating a confidence level into an electrophysiological ("EP") map, the system comprising:
a processor, which is configured to:
receive a modeled surface of at least a portion of a heart and multiple EP values measured at multiple respective positions in the heart;
define multiple regions on the modeled surface;
calculating a median EP value for each of the multiple regions based upon the measured EP values whose positions fall in the region;
estimate a confidence level for each of the median EP values;
cause the modeled surface to be displayed to a user, including median EP values overlaid on the modeled surface, and respective graphically visualizing the confidence levels for the EP values at each region of the modeled surface;
identify each region of the multiple regions having a confidence level lower than a predefined threshold level;
acquire one or more additional EP values at additional locations within each region having confidence levels lower than the threshold; and
use the one or more additional EP values to recalculate the median EP value and confidence level for the recalculated median EP value for each region having confidence levels lower than the threshold until the respective confidence level for each region equals or exceeds the threshold.

13. The system according to claim 12, wherein the processor is configured to estimate the confidence level by calculating the confidence level depending on a count of the EP values falling in the region.

14. The system according to claim 12, wherein the processor is configured to estimate the confidence level for a region by calculating the confidence level as an increasing function of a count of the EP values falling in the region.

15. The system according to claim 12, wherein the processor is configured to estimate the confidence level for a region by calculating the confidence level as a decreasing function of a variance of a distribution of the EP values falling in the region.

16. The system according to claim 12, wherein the interface is configured to receive the EP values from a catheter.

17. The system according to claim 12, wherein the modeled surface is a surface generated by fast anatomical mapping (FAM).

18. The system according to claim 12, wherein the EP values are one of local activation times (LATs), bipolar potentials, and unipolar potentials.

19. The system according to claim 12, wherein the processor is configured to graphically visualize the confidence levels by presenting, at the regions, respective icons whose sizes are an increasing function of the respective confidence levels.

20. The system according to claim 12, wherein the processor is further configured to project multiple positions onto multiple locations in the region, and assign the EP values at the positions to the respective locations.

21. The system according to claim 12, wherein the regions comprise polygons in a polygonal mesh of the modeled surface.

22. The system according to claim 12, wherein one or more of the regions are circular areas having a predefined radius.

23. A computer program product, comprising a non-transitory computer-readable medium having computer-readable program code embodied therein to be executed by one or more processors, the program code including instructions to:
receive a modeled surface of at least a portion of a heart and multiple EP values measured at multiple respective positions in the heart;
define multiple regions on the modeled surface;
calculate a median EP value for each of the multiple regions based upon the measured EP values whose positions fall in the region;
estimate a confidence level for each of the median EP values;
cause the modeled surface to be displayed to a user, including median EP values overlaid on the modeled surface, and respective graphically visualizing the confidence levels for the EP values at each region of the modeled surface;
identify each region of the multiple regions having a confidence level lower than a predefined threshold level;
acquire one or more additional EP values at additional locations within each region having confidence levels lower than the threshold; and
use the one or more additional EP values to recalculate the median EP value and confidence level for the recalculated median EP value for each region having confidence levels lower than the threshold until the respective confidence level for each region equals or exceeds the threshold.

24. The computer program product according to claim 23, wherein estimating the confidence level comprises calculating the confidence level depending on a count of the EP values falling in the region.

25. The computer program product according to claim 23, wherein estimating the confidence level for a region comprises calculating the confidence level as an increasing function of a count of the EP values falling in the region.

26. The computer program product according to claim 23, wherein estimating the confidence level for a region comprises calculating the confidence level as a decreasing function of a variance of a distribution of the EP values falling in the region.

* * * * *